United States Patent [19]

Sanderson et al.

[11] 4,420,625

[45] Dec. 13, 1983

[54] ALKYLENE OXIDES PRODUCED BY DIRECT OXIDATION OF OLEFINS OVER TRANSITION METAL BORATES IN THE PRESENCE OF A NON-POLAR, AROMATIC ORGANIC SOLVENT

[75] Inventors: John R. Sanderson; Walter H. Brader, Jr.; Lewis W. Watts, Jr., all of Austin, Tex.

[73] Assignee: Texaco, Inc., White Plains, N.Y.

[21] Appl. No.: 421,925

[22] Filed: Sep. 23, 1982

[51] Int. Cl.$^3$ ............................................ C07D 301/06
[52] U.S. Cl. .................................................... 549/533
[58] Field of Search ......................................... 549/533

[56] References Cited

U.S. PATENT DOCUMENTS 4,256,650  3/1981  Bljumberg et al. .................. 549/533

FOREIGN PATENT DOCUMENTS 2255510  5/1974  Fed. Rep. of Germany ...... 549/533

Primary Examiner—Norma S. Milestone
Attorney, Agent, or Firm—Jack H. Park; Kenneth R. Priem; David L. Mossman

[57] ABSTRACT

A process for the production of alkylene oxides from olefins in the presence of transition metal borate catalysts, oxygen and a non-polar, aromatic organic solvent via one-step, direct oxidation is described. The reaction is conducted at a temperature in the range of 80° to 280° C. and a pressure of 1 atmosphere or greater. Alkylene oxides have a variety of uses such as in polyols for urethane foams, the production of alkylene glycols, surfactants and detergents, alkanolamines, fumigants, synthetic lubricants and elastomers.

16 Claims, No Drawings

ALKYLENE OXIDES PRODUCED BY DIRECT OXIDATION OF OLEFINS OVER TRANSITION METAL BORATES IN THE PRESENCE OF A NON-POLAR, AROMATIC ORGANIC SOLVENT

CROSS-REFERENCES TO RELATED APPLICATION

This application is related to U.S. patent application Ser. No. 402,664, which relates to a method for producing alkane acetates by oxidative esterification of olefins over transition metal borate catalysts in the presence of acetic anhydride.

BACKGROUND OF THE INVENTION

1. Field of the Invention

The invention is related to a process for the production of alkylene oxides by the direct oxidation of olefins, and is particularly related to such a process conducted in the presence of a non-polar, aromatic organic solvent and a transition metal borate catalyst.

2. Description of Relevant Methods

The production of ethylene oxide from ethylene has long been known. However, there has been a less successful search for a similar process for producing propylene oxide directly from propylene in an economic manner. The same processes which produced ethylene oxide cannot be adapted to the production of propylene oxide.

As a result, a number of different schemes to produce propylene oxide from propylene or to produce an intermediate to propylene oxide from propylene have been proposed. Initially the research effort seemed to be directed to producing an olefin oxide directly from the olefin in the presence or absence of a solvent. U.S. Pat. No. 2,649,463 describes the production of a coordination complex created by the reaction of an olefin with a metal halide where the metal is copper, platinum, palladium, iridium, aluminum, zinc, silver, mercury or antimony. This coordination complex is further reacted with oxygen at a high temperature to produce the olefin oxide plus oxygen-containing metal halides. Hawkins, et al. in an article entitled, "Autoxidation of Olefins," in the *Journal of Applied Chemistry*, Vol. 6, 1956, pgs 1 through 10, describes a process for the production of epoxides directly from olefins and molecular oxygen over magnesium oxide and/or cobalt naphthenate. The direct production of olefin oxides from a mono olefin and a saturated hydrocarbon with oxygen and water, organic acids or olefin oxide in low concentration is described in U.S. Pat. No. 2,780,634.

British Pat. No. 1,582,261 describes how propylene may be reacted with oxygen over a dinitrogen tetraoxide catalyst in a liquid medium of a chlorinated organic solvent to produce propylene oxide directly. Propylene oxide may also be prepared directly from propylene and oxygen over a catalyst system comprising a palladium cation plus a chloride anion in the presence of a phosphorous or arsenic ligand as revealed in U.S. Pat. No. 4,256,649.

Further, U.S. Pat. No. 2,784,202 outlines how propylene in a liquid hydrocarbon solvent, such as benzene, in the presence of oxygen and water, organic acids or propylene oxide in low concentration yield propylene oxide when heated at a temperature between 130° and 300° C. Propylene oxide is also proposed to be made directly from propylene in benzene in the presence of oxygen over a cobalt, copper, magnesium, vanadium or chromium catalyst where barium or lead is used as a promoter for the catalyst, according to U.S. Pat. No. 3,071,601. Brill, et al. in *Journal of Organic Chemistry*, Vol. 29, 1964, pgs 140–143, describes a process for passing olefins and oxygen, frequently in contact with or dissolved in benzene over various catalysts such as azobisisobutyronitrile, cadmium oxide, cobaltic acetylacetonate, magnesium oxide or methyl ethyl ketone peroxide to produce various oxidation products, including the desired epoxides. U.S. Pat. No. 3,132,156 reveals that ethylene, propylene or butylene oxide may be produced directly from ethane, propane or butane under very precise conditions. These conditions include a temperature of between 425° to 575° C., an oxygen volume percent of between 4 and 14, a contact time with the oxygen of between 0.07–1.5 seconds, a pressure of between 20 to 150 psig and constant concentrations of reactants. Epoxides may also be produced from olefins and oxygen which are in an inert reaction medium when they are brought in contact with a rhenium catalyst and 0.05 to 15 weight percent of a reaction modifier comprised of an alkyl aryl or cyclo alkyl cyanide, pyridine or quinoline in accordance with the invention described in U.S. Pat. No. 3,316,279.

Other schemes for producing olefin oxides from olefins and oxygen by means of a solvent or liquid reaction medium include the following. U.S. Pat. No. 3,153,058 employs polyacyl esters of polyhydroxy alkanes, polyhydroxy cycloalkanes, polyglycols or mixtures thereof as the solvent. Materials selected from saturated aliphatic, alicyclic and aromatic nitriles and mixtures thereof form the solvent in U.S. Pat. No. 3,210,380. Boric acid esters form the liquid reaction medium in U.S. Pat. No. 3,210,381. U.S. Pat. No. 3,228,967 uses major amounts of acetone as the solvent. Carbonic acid esters are employed in U.S. Pat. No. 3,228,968, and at least 25 percent by weight of certain ketones serves as the reaction medium in U.S. Pat. No. 3,232,957. Halogenated benzenes serve as the solvent in U.S. Pat. No. 3,238,229 while benzoic acid esters are employed in a similar reaction described in U.S. Pat. No. 3,281,433. Olefin oxides may be prepared directly from olefins and oxygen over a hydrocarbon soluble, phosphorous molybdenum-hydroxy compound catalyst according to the disclosure in U.S. Pat. No. 3,856,826. The approach of making epoxides directly has never been commercially feasible because all of the methods explored gave low yields of epoxides.

Other schemes work somewhat differently from those described above. U.S. Pat. No. 4,237,331 reveals that olefins may be reacted with oxygen in the presence of a suitable surfactant and a diluent over a palladium/copper/boric acid catalyst to produce carbonyl compounds. Propylene may be reacted with acetaldehyde and oxygen in the presence of a boron-containing compound which also has a metal from Groups IVB, VB or VIB of the Periodic Table to give propylene oxide and acetic acid, according to the teaching of U.S. Pat. No. 4,256,650. However, the mechanism to the propylene oxide in this method apparently goes through a peracid intermediate which is not present in the mechanism of the present method. U.S. Pat. No. 3,071,601 instructs that propylene may be reacted with oxygen over a cobalt, copper, manganese, vanadium or chromium catalyst with barium or lead as a promoter to give propylene oxide.

French Pat. No. 1,386,354 reveals the oxidation of olefins with oxygen in the presence of a solvent partially miscible with water and a cobalt catalyst at elevated temperatures and pressures. Finally, British Pat. No. 1,037,946 teaches a method of oxidizing propylene in gas or liquid phase over a silicon-based catalyst such as a silicic ester.

Despite all of the investigative routes described so far and the ones that have been devised which have not been described, there is still a need for an efficient method for making propylene oxide from propylene, in addition to making the alkylene oxides from other olefins, which does not involve a highly corrosive or highly expensive catalyst system.

SUMMARY OF THE INVENTION

The invention concerns a process for the production of alkylene oxides comprising reacting an olefin or a mixture of olefins with oxygen in the presence of a transition metal borate catalyst and a non-polar, aromatic organic solvent.

DETAILED DESCRIPTION OF THE PREFERRED EMBODIMENTS

Alkylene oxides may be prepared by the oxygen or air oxidation of olefins in a non-polar, aromatic organic solvent in the presence of a transition metal borate catalyst. The process is particularly advantageous because it can produce alkylene oxides directly, in one step. The epoxides are of interest in the manufacture of important high volume products, including urethane polyols, alkylene glycols, surfactants and detergents, alkanolamines, fumigants, synthetic lubricants, gasoline additives and elastomers.

According to the method of this invention, the olefin feedstocks may consist of any mono olefin having the double bond located anywhere within the molecule and mixtures of such olefins. The olefin may be an alpha or an internal olefin. Specific examples of suitable feedstocks include, but are not limited by, the following list: propylene, 1-butene, 2-butene, 1-pentene, 2-pentene, 1-hexene, 2-hexene, 3-hexene, heptenes, octenes, nonenes, decenes, undecenes, dodecenes, tridecenes such as 6-tridecene, tetradecenes such as 7-tetradecene, pentadecenes, hexadecenes, etc., and mixtures thereof. Preferably, the olefin has 3 to 16 carbon atoms.

Of course, molecular oxygen in a pure form or air is an essential co-reactant for the method of this invention.

The co-reactant and solvent must be a compound that is inert with respect to the oxidation reaction. These compounds may be generally described as non-polar, aromatic organic solvents. Suitable solvents are halobenzenes and alkylbenzenes. Specific, preferred solvents are chlorobenzene and dibutyl phthalate.

Catalysts found to be useful in the method of this invention include transition metal borates. Borate compounds are believed to be novel for the catalysis of olefins to alkylene oxides directly, never having been previously discovered. Transition metals are defined as those of Groups IIIB, IVB, VB, VIB, VIIB, VIII, IB and IIB of the Periodic Table. Preferred borates include borates of Group VIII transition metals. Especially preferred borates include nickel borate, copper borate and iron borate, particularly nickel borate. These catalysts are much less corrosive than many of these used in other methods, especially the halide systems. Also, much smaller catalyst levels may be used. They are also less expensive than many of the catalyst systems proposed.

The reaction conditions under which the method of this invention may be conducted include a temperature range of from 80° to 280° C. A preferred range is from 120° to 220° C. The pressure may be one atmosphere or higher. Due to the use of the borate catalyst, these conditions are much milder than many of those in the prior art discussed earlier. Surprisingly, no period of inhibition or induction is observed in the method of this invention, even at lower temperatures, unlike prior art methods which would lengthen the reaction time.

The invention will be further illustrated by the following examples which are not intended to limit the scope of the invention.

EXAMPLE 1

Three hundred ml of chlorobenzene and 1.0 g of nickel borate catalyst were added to a 1-liter glass-lined autoclave equipped with a magnetic stirrer. The autoclave was sealed. Propylene (84 g) was pressured into the reactor and the contents heated to 160° C. The autogeneous pressure was 440 psig. The reactor was pressured slowly to 500 psig and held at 500 psig (by repressuring with oxygen from time to time) for three hours. A mild exotherm was noted after each addition of oxygen. The mixture was cooled to room temperature, the propylene vented and the chlorobenzene analyzed by vapor phase chromatography (VPC). Propylene oxide (3.4 g) was obtained. In addition, small quantities of acetaldehyde, formaldehyde, acetic acid and formic acid were also formed.

EXAMPLE 2

The procedure, mole ratios, etc. were essentially the same as in Example 1. The reaction was conducted at 140° C. for three hours. VPC analysis indicated 2.9 g of propylene oxide. In addition, small quantities of acetaldehyde, formaldehyde, acetic acid and formic acid were also formed.

EXAMPLE 3

In this example, dibutyl phthalate was substituted as the aromatic solvent. Three hundred ml of dibutyl phthalate and 1.0 g of nickel borate were charged to a 1-liter glass-lined autoclave equipped with a magnetic stirrer. The autoclave was sealed. Propylene (84 g) was pressured into the reactor and the contents heated to 140° C. The autogeneous pressure was 500 psig. The reactor was pressured to 500 psig and held at 560 psig (by repressuring from time to time) for three hours. The mixture was cooled to room temperature, the propylene vented and the dibutyl phthalate analyzed by VPC. A yield of 1.2 g of propylene oxide was indicated. In addition, small quantities of acetaldehyde, formaldehyde, acetic acid and formic acid were also formed.

EXAMPLE 4

The procedure, quantities, etc. were the same as Example 3. The reaction was conducted at 150° C. for three hours. VPC analysis indicated 3.0 g of propylene oxide. In addition, small quantities of acetaldehyde, formaldehyde, acetic acid and formic acid were also formed.

EXAMPLE 5

The procedure, quantities, etc. were the same as Example 3. The reaction was conducted at 160° C. for three hours. VPC analysis indicated 4.0 g of propylene oxide. In addition, small quantities of acetaldehyde, formaldehyde, acetic acid and formic acid were also formed.

It is noteworthy that *Kogyo Kagaku Zasshi,* 67, 1026–1031 (1964) indicates that the oxidation of propylene in the presence of metal naphthenates (a typical catalyst) has an induction period of twelve hours (at 145° C.). Such a lengthy induction period is not necessary in the method of this invention.

Many modifications may be made in the method of this invention by those skilled in the art to maximize the yields of the desirable oxides without departing from the spirit and scope of the invention which is defined only by the appended claims. For example, one skilled in the art could determine an exact combination of transition metal borate catalysts, temperatures, solvents and modes of addition to optimize the yield.

We claim:

1. A process for the production of alkylene oxides comprising reacting an olefin or a mixture of olefins with oxygen in the presence of a transition metal borate catalyst and a non-polar, aromatic organic solvent.

2. The process of claim 1 in which the reaction is conducted at a temperature in the range of 80° to 280° C.

3. The process of claim 2 in which the reaction is conducted at a temperature between 120° and 220° C.

4. The process of claim 1 in which the olefins have 3 to 16 carbon atoms.

5. The process of claim 1 in which the olefin is propylene.

6. The process of claim 1 in which the solvent is selected from the group of solvents consisting of chlorobenzene and dibutyl phthalate.

7. The process of claim 1 in which the transition metal in the borate catalyst is taken from the group consisting of nickel, copper and iron.

8. The process of claim 1 in which the catalyst is nickel borate.

9. A process for the production of alkylene oxides comprising reacting an olefin or a mixture of olefins with oxygen in the presence of a transition metal borate catalyst where the transition metal is selected from the group consisting of nickel, copper and iron, and a non-polar, aromatic organic solvent, the reaction being conducted at a temperature in the range of 80° to 280° C.

10. The process of claim 9 in which the reaction is conducted at a temperature between 120° and 220° C.

11. The process of claim 9 in which the olefins have 3 to 16 carbon atoms.

12. The process of claim 9 in which the solvent is selected from the group of solvents consisting of chlorobenzene and dibutyl phthalate.

13. A process for the production of alkylene oxides comprising reacting an olefin or a mixture of olefins where each molecule has 3 to 16 carbon atoms, with oxygen in the presence of a non-polar, aromatic organic solvent selected from the group consisting of chlorobenzene and dibutyl phthalate and a transition metal borate catalyst where the transition metal is selected from the group consisting of nickel, copper and iron, and at a temperature in the range of 80° to 280° C.

14. The process of claim 13 in which the reaction is conducted at a temperature between 120° and 220° C.

15. The process of claim 13 in which the olefin is propylene.

16. A process for the production of alkylene oxides comprising reacting propylene with oxygen in the presence of a non-polar, aromatic organic solvent selected from the group consisting of chlorobenzene, dibutyl phthalate and nickel borate at a temperature in the range of 120° to 220° C.

* * * * *